United States Patent [19]
Cha et al.

[11] Patent Number: 5,665,428
[45] Date of Patent: Sep. 9, 1997

[54] PREPARATION OF PEPTIDE CONTAINING BIODEGRADABLE MICROSPHERES BY MELT PROCESS

[75] Inventors: Younsik Cha; Young Kweon Choi, both of Salt Lake City, Utah; Chaul Min Pai, Taejon, Rep. of Korea

[73] Assignee: Macromed, Inc., Salt Lake City, Utah

[21] Appl. No.: 547,962

[22] Filed: Oct. 25, 1995

[51] Int. Cl.$^6$ .............................. B01J 13/02; B05D 7/00
[52] U.S. Cl. .................. 427/213.3; 427/213.34; 427/213.36
[58] Field of Search ................ 427/213.3, 213.34, 427/213.36

[56] References Cited

U.S. PATENT DOCUMENTS

| | | | |
|---|---|---|---|
| 4,438,253 | 3/1984 | Casey et al. | 528/86 |
| 4,526,938 | 7/1985 | Churchill et al. | 525/415 |
| 4,652,441 | 3/1987 | Okada et al. | 424/19 |
| 4,745,160 | 5/1988 | Churchill et al. | 525/415 |
| 4,938,763 | 7/1990 | Dunn et al. | 604/891.1 |
| 5,100,669 | 3/1992 | Hyon et al. | 427/213.36 |
| 5,278,202 | 1/1994 | Dunn et al. | 523/113 |
| 5,324,519 | 6/1994 | Dunn et al. | 424/426 |
| 5,330,768 | 7/1994 | Park et al. | 424/501 |
| 5,418,010 | 5/1995 | Janda et al. | 427/213.31 |

FOREIGN PATENT DOCUMENTS

| | | |
|---|---|---|
| 0 092 918 | 3/1983 | European Pat. Off. . |
| 0 258 780 | 8/1987 | European Pat. Off. . |
| 2-78629 | of 1990 | Japan . |
| WO/93/24150 | 5/1992 | WIPO . |

OTHER PUBLICATIONS

"Inulin Disposition Following Intramuscular Administration of an Inulin/Poloxamer Gel Matrix" Thomas P. Johnston and Susan C. Miller; Journal of Parenteral Science & Technology vol. 43, No. 6/Nov.–Dec. 1989.

"Sustained Delivery of Interleukin–2 from a Poloxamer 407 Gel Matrix Following Intraperitioneal Injection in Mice" Thomas P. Johnston, Monika A. Punjabi, and Christopher J. Froelich; Pharmaceutical Research, vol. 9 No. 3, 1992.

"Bioerodible Hydrogels Based on Photopolymerized Poly(ethyleneglycol)–co–poly(α–Hydroxyacid) Diacrylate Macromers" Amarpreet S. Sawhney, Chandrashekhar P. Pathak, and Jeffrey A. Hubbell; Macromolecules, vol. 26, No. 4, 1993.

"Angiopeptin as a Potent Inhibitor of Myointimal Hyperplasia" Takehisa Matsuda, Noboru Motomura and Takashi Oka; ASAIO Journal 1993.

"Micellisation and Gelation of Triblock Copolymer of Ethylene Oxide and εCaprolactone, $Cl_nE_mCl_n$, in Aqueous Solution," Lugi Martini, David Attwood, John H. Collette, Christian V. Nicholas, Siriporn Tanodekaew, Nan–Jie Deng, Frank Heatley and Colin Booth; J. Chem. SOC. Faraday Trans. 1994.

"Enhancement of Therapeutic Effects of Recombinant Interleukin 2 on a Transplantable Rat Fibrosarcoma by the Use of a Sustained Release Vehicle, Pluronic Gel." Kiyoshi Morikawa, Futoshi Okada, Masuo Hosokawa, and Hiroshi Kobayashi;Caner Research 47, 37–41, Jan. 1, 1987.

"Toxicological Evaluation of Poloxamer Vehicles for Intramuscular Use." Thomas P. Johnston and Susan C. Miller; Journal of Parenteral Science and technology vol. 39, No. 2/Mar.–Apr. 1985.

"In–vitro degradation and bovine serum albumin release of the ABA triblock copolymer consisting of poly (L(+)lactic acid), or poly (L(+)lactic acid–co–glycolic acid) A–blocks attached to central polyoxyethylene B–blocks" Li Youxin, Christian Volland, Thomas Kissel; Journal of Controlled Release 32 (1994).

"Synthesis and properties of biodegradable ABA triblock copolymers consisting of poly (L–lactic acid) or poly (L–lactic–co–glycolic acid) A–blocks attached to central poly (oxyethylene) b–blocks" Li Youxin and Thomas Kissel; Journal of Controlled Release, 27 (1993).

"Sustained–Release of Urease from a Poloxamer Gel Matrix", K.A. Fults and T.P. Johnston; Journal of Parenteral Science & Technology vol. 44, No. 2/Mar.–Apr. 1990.

*Primary Examiner*—Nathan M. Nutter
*Attorney, Agent, or Firm*—Thorpe, North & Western, L.L.P.

[57] ABSTRACT

Peptide/protein biodegradable drug delivery devices are prepared as microspheres without the use of solvents by a polymer melt process. A melt of thermostable polypeptides and an appropriate low melting block copolymer mixture is prepared and dispersed in an appropriate fluid medium such as air, water or an immiscible organic fluid without using any organic solvent to form microdroplets. The fluid medium is cooled to solidify the microdroplets into microspheres and then collected and purified or further processed as drug delivery devices. These biodegradable microspheres are suitable as implantable or injectable pharmaceutical formulations. Following administration as solid microspheres into the body of a warm blooded animal, the formulations absorb water from the body to form a hydrogel from which the polypeptide is released continuously over an extended period of time.

24 Claims, No Drawings

PREPARATION OF PEPTIDE CONTAINING BIODEGRADABLE MICROSPHERES BY MELT PROCESS

The present invention relates to biodegradable microspheres containing peptide or protein drugs and to methods for their preparation. More particularly, this invention relates biodegradable microspheres containing peptide or protein drugs and to a melt process for preparing the same. This invention is made possible by the use of thermoplastic biodegradable hydrogels of relatively low melting temperature, which are described in detail hereinafter. It is based on the discovery that peptides and proteins exhibit superior solid-state stability in low aqueous or non-aqueous environments and also on the discovery that solid proteins embedded within certain thermoplastic polymeric systems exhibit superior stabilities when compared with their behavior under otherwise identical conditions in aqueous solutions. This invention further relates to a method of making biodegradable microspheres without using any organic solvents by employing suitable low melting temperature biodegradable polymers specifically designed for this purpose.

BACKGROUND OF THE INVENTION AND SUMMARY OF PRIOR ART

Numerous synthetic and natural polymers are known to be available as matrices for controlled drug delivery systems (DDS) such as implants, microcapsules and micro- and/or nanospheres. Some of these polymers are non-biodegradable, for example polymethyl methacrylate (PMMA), polystyrene(PST), ethylene-vinyl acetate copolymer(EVA), polyethylene-maleic anhydride copolymers and polyamides. In the case of non-biodegradable polymers, a drug carrying polymeric implant or pellet utilizing any of these polymers has to be removed at the end of the release period. To avoid the necessity of removal and problems associated therewith it has been found desirable to develop controlled drug release polymeric devices based on biodegradable or bioerodible polymers. The use of biodegradable polymers avoids the removal of the device from the site of administration after the depletion of the drug. Biodegradable polymers can be designed to degrade in vivo in a controlled manner over a predetermined time period. Suitable biodegradable polymers for use in such sustained release formulations are well described elsewhere and include polyesters such as poly(d,l-lactide), poly(d,l-lactide-co-glycolide), poly (ε-caprolactone), poly (hydroxybutylic acid) and poly (aminoacids), poly (orthoesters), polyanhydrides and polyalkyl cyanoacrylates. These polymers gradually become degraded by enzymatic or non-enzymatic hydrolysis when placed in an aqueous, physiological environment. The main mechanism of in vivo degradation of polymers is hydrolytic degradation in which enzymes may also play a role. Important factors influencing hydrolytic degradation include water permeability, chemical structure, molecular weight, morphology, glass transition temperature, additives, and other environmental factors such as pH, ionic strength, site of implantation, etc.

Various microencapsulation techniques incorporating a drug into a biodegradable polymer matrix are taught in the art. Exemplary of these are: (a) phase separation by emulsification and subsequent organic solvent evaporation (including complex emulsion methods such as O/W emulsions, W/O emulsions and W/O/W emulsions); (b) coacervation-phase separation; (c) melt dispersion; (d) interfacial deposition; (e) in situ polymerization; (f) spray drying and spray congealing; (g) air suspension coating; and (h) pan coating. As exemplified in U.S. Pat. No. 4,652,441, a W/O/W (water/oil/water) double emulsion in-water drying process is a commonly used method for microencapsulation of water-soluble hydrophilic drugs such as peptides and proteins. However, this procedure presents various technical problems in preparation of microspheres and their use. For example, there is a requirement that a third component, such as gelatin, must be present in addition to the drug and the polymer utilized, e.g., a polylactic acid polymer. It is difficult to obtain microspheres in submicron order and there is a low rate of incorporation of the drug into capsules due to three-layer (W/O/W) structure. Moreover, there is an unstable release of the drug from the microspheres beginning with a burst effect induced by damage to, or rupture of, the thin polylactic acid wall of the microsphere.

U.S. Pat. No. 5,100,669 is drawn to polylactic acid type microspheres containing physiologically active substances and to a process for preparing the same. It is advantageous in that the active substance can be uniformly incorporated into the microspheres without loss of the activity and can gradually release the active substance for a long period of time of more than one week. In this patent there is taught the preparation of microspheres wherein the hydrophilic physiologically active substance and hydrophobic polylactic acid are uniformly mingled in a molecular order. By using a co-solvent such as acetonitrile-water mixtures or glacial acetic acid for the oligomeric polylactides and various drugs including peptides and proteins, the active substance can be uniformly incorporated into the microspheres without loss of activity and sustained release can be achieved without significant initial burst. However, in order to obtain the microspheres the use of an organic solvent is required.

U.S. Pat. No. 4,526,938 discloses the use of amphipathic, non-crosslinked, branched or graft block copolymers which have a minimum weight average molecular weight of 5,000 as carriers for the continuous release of polypeptide drugs. The hydrophobic block component, such as polylactide, is biodegradable and the hydrophilic block component, such as polyethylene glycol, may or may not be biodegradable. Such copolymeric compositions are capable of absorbing water to form a hydrogel when placed in an aqueous, physiological type environment. The use of an organic solvent is required which can be denaturing to polypeptides. U.S. Pat. No. 4,745,160 discloses a similar type of copolymer which has a minimum weight average molecular weight of 1,000 and is self-dispersible in water. Such copolymers are also useful for the sustained release of polypeptide drug formulations. The dosage forms in this patent are obtained by freeze drying a dispersion of a mixture of copolymer and peptide drug to obtain a powder. The powder is then subjected to heat and pressure to prepare a dosage form by compression moulding.

Hutchinson (WO 93/24150) teaches salts composed of a cation derived from a peptide containing at least one basic group and an anion derived from a carboxy-terminated polyester. The polyester is selected from those derived from hydroxy-acids or polycondensation products of diols and/or polyols with dicarboxylic acid and/or polycarboxylic acids. Typically, the polymer is a d,l-lactide/glycolide copolymer having one terminal carboxylic acid group per polymer chain. A process for the manufacture of such salts and their use as extended release pharmaceutical compositions are also disclosed. Typically, the peptide and carboxylic acid polymer are mixed in glacial acetic acid and lyophilized. The freeze dried product is then added to dichloromethane and solvent cast to obtain a film. Hutchinson then describes the use of the film in polymer melt-processing techniques, such as extrusion, and compression and injection molding, wherein elevated temperatures (preferably less than 100° C.) are used to melt the polyester-drug salt in the preparation of an implant. Such solid dosage forms can be reduced to microparticulate forms by comminution or milling. Hutchinson contains an excellent discussion on polymeric hydrophobic/hydrophilic component and drug incompatibilities and other problems associated with the formation of microspheres using various solvents in dispersion or freeze drying techniques and is therefore incorporated herein by reference.

European Patent Application 0258780 A2 describes drug delivery systems (DDS) made up of ABA or AB block copolymers wherein one block is a poly(alkylene oxide) and the other blocks are glycolic acid ester/trimethylene carbonate. It describes the coextrusion of the polymers and a biologically active material at 60°–115° C. on a laboratory scale extruder. The ratio of active material is chosen to be 1–50% w/w but is preferably 25–50% w/w. The 1.5 mm diameter fibers can be cut into lengths or cryogenically ground through a 20 mesh screen to give particles which are capable of being injected, or the fiber can be directly implanted.

U.S. Pat. No. 4,438,253 describes multiblock copolymers obtained by transesterification of polyglycolic acid and hydroxyl-ended poly(alkylene glycol) such as polyoxyethylene and subsequent addition of an aromatic orthocarbonate such as tetra-p-tolyl orthocarbonate to further increase the degree of polymerization. Those materials were used for manufacturing surgical articles and a hydrolyzable monofilament fiber.

The release of a polypeptide from a polylactide polymer is often preceded by a significant induction period, during which no polypeptide is released, or is polyphasic which comprises an initial burst release from the surface of the device, a second period during which little or no polypeptide is released, and a third period during which most of the remainder of the polypeptide is released.

Various attempts have been made to solve or at least minimize this problem and improve the release profile. One method is to copolymerize lactic acid with glycolic acid to form poly(lactide-glycolide) copolymers. Another is to mix a peptide encapsulated in polylactide polymer with the same peptide encapsulated in other polymers or copolymers. Both of these methods are difficult to control during manufacture and administration and have not been totally successful in achieving the desired peptide release rate.

One attempt to solve the release rate problem is presented in U.S. Pat. No. 5,330,768. This patent discloses degradable polymeric matrices prepared by the physical blending of biodegradable hydrophobic polymers, such as polylactides, with nonionic hydrophilic copolymers, such as surfactant block copolymers of polyethyleneoxide (PEO) and polypropyleneoxide (PPO). Protein or peptide drugs are incorporated into the polymeric blends by mechanical mixing, or by solvent or melt casting. In aqueous solutions, these polymeric blends allegedly form gel like structures within a polymeric skeleton which provide for extended protein release and minimized initial protein burst as compared to the pure polylactide polymers. However, when polymer blends are prepared as microspheres, a modified solvent evaporation technique using double emulsion is employed which requires the use of solvents such as methylene chloride which must be evaporated into the surrounding atmosphere.

In vitro release of bovine serum albumin (BSA) from ABA triblock copolymers consisting of copoly(l-lactic acid-b-oxyethylene-b-l-lacticacid) (LPLA-PEO-LPLA) and copoly(l-lactic-co-glycolic acid-b-oxyethylene-b-l-lactic-co-glycolic acid)(LPLG-PEO-LPLG) as microspheres was studied by Youxin et al., J. Controlled Release 32 (1994) 121–128. However, the microspheres were prepared by a triple emulsion technique which employs an organic solvent such as methylene chloride. Continuous release of protein can be obtained by adjusting the composition of such ABA triblock copolymers. The introduction of hydrophilic PEO blocks into hydrophobic polyesters should promote effective water uptake and should also increase the permeability of parenteral delivery systems especially for water soluble drugs such as peptides and proteins. Both molecular weight decay and mass loss are accelerated in such ABA block copolymers by the rapid penetration of water into the microphase-separated system. Depending on PEO content and polyester ratio degradation rates can be adjusted. The release of polypeptides from the matrix of ABA block copolymers is controlled by the diffusion of the drug in the swollen matrix as well as by the degradation of the matrix.

Implantable polymeric drug delivery systems have been known for some time. A unique aspect of ABA type copolymer formulations, such as those disclosed by R. L. Dunn et al., U.S. Pat. No. 4,938,763 and 5,278,202, is the fact that when formulated, they maintain a liquid consistency which allows injection using 22/23 gauge needle. Once in contact with aqueous fluid the copolymeric network absorbs the fluid and sets into a gel matrix. The overall triblock copolymer composition can be manipulated to have a degradation time in the range of days, weeks or months. Depending upon the polymeric blocks used, i.e. polymer type, molecular weight, relative proportions, etc, the degradation rate can be adjusted by choosing the appropriate polymeric block components. These block copolymers are generally non-toxic and are well tolerated by the body and the system is easy to formulate. Drug laden copolymers of lactic and/or glycolic acids and ethylene oxide provide a fresh approach for a biodegradable implant since they can be easily injected, avoiding the use of surgical procedures. A gel matrix, similar to an implant, is formed immediately after injection on contact with an aqueous environment of extracellular fluid and the release of the drug takes place slowly through this formed matrix. The in vivo degradation rate of the copolymers, such as those of lactic and/or glycolic acids and polyethyleneoxide, can be controlled by using different mole ratios of the constituent monomers and molecular weight of copolymers. Their biocompatibility and biodegradability is also well established. The gel matrix once formed will release the drug in a controlled manner and then degrade to products which are easily metabolized and excreted. This approach incorporates the advantages of a drug delivery device implant while circumventing the need for surgery to place the implant prior to administration or remove it after the release is complete. However, the major drawback in the preparation of these copolymers is the use of undesirable and sometimes toxic organic solvents such as N-methyl-2-pyrrolidone, dimethyl sulfoxide, ethyl lactate, triacetin and triethyl citrate. These solvents are used because they can dissolve the polymer components and are also miscible with water.

Primarily due to the development of DNA-recombinant techniques, peptide and protein drugs are becoming more and more available in a large scale. However, because of the relatively short biological half-life of protein drugs and their rapid degradation by proteolytic enzymes in the gastrointestinal tract, repeated daily injections are generally needed to optimize drug effectiveness. Among many new DDS devices, injectable drug containing polymeric microsphere systems can provide a means for the safe and controlled parenteral administration of peptides and proteins. However, the formulation and delivery of these relatively high molecular weight peptide and protein drugs can present certain problems due to their relatively fragile nature when compared to traditional, smaller molecular weight drugs. In order to successfully employ polypeptides as pharmaceuticals, it is essential to understand the stability issues relevant to their formulation and delivery. Polypeptides undergo a variety of intra and intermolecular chemical reactions which can lead to their decline or loss of effectiveness as pharmaceuticals. These include oxidation, deamidation, β-elimination, disulfide scrambling, hydrolysis, isopeptide bond formation, and aggregation. In addition to chemical stability, polypeptides must also retain their three dimensional structure in order to be effective therapeutic agents. Loss of this native conformation leads not only to loss of biological activity but also to increased susceptibility to further deleterious processes such as covalent or noncovalent aggregation. Furthermore, the large size of protein aggregates leads to other problems relating to parenteral delivery, such as decreased solubility and increased immunogenicity. H. R. Costantino et al., J. Pharm. Sci., 83, (1994) 1662–1669 "Solid-phase aggregation of proteins under pharmaceutically relevant conditions."

By knowing the various molecular pathways which contribute to aggregation of solid proteins, rational approaches for stabilization can be developed. The first approach is to specifically target the mechanisms involved. A second approach is to maintain the level of moisture activity within the protein at optimal levels. This may be achieved by storing the protein at optimal hydration levels or, in the case of sustained release devices, by choosing a microenvironment that will ensure lower water activities. The pH of the microenvironment can also be controlled. A third approach for stabilizing solid protein formulations is to increase the physical stability of lyophilized protein. This will inhibit aggregation via hydrophobic interactions as well as via covalent pathways which may increase as proteins unfold.

The providing of a functional biodegradable hydrogel microsphere system is very desirable from a protein stability point of view. As noted above, the critical role of water in protein structure, function, and stability is well known. Typically, proteins are relatively stable in the solid state with bulk water removed. However, solid therapeutic protein formulations may become hydrated upon storage at elevated humidities or during delivery from a sustained release device. The stability of protein drops with increasing hydration. Water can also play a significant role in solid protein aggregation for various reasons, i.e., (a) it increases protein flexibility resulting in enhanced accessibility of reactive groups; (b) it is the mobile phase for reactants and (c) it itself is a reactant in several deleterious processes such as β-elimination or hydrolysis. Proteins containing between 6% to 28% water are the most unstable. Below this level, the mobility of bound water and protein internal motions are low. Above this level, water mobility and protein motions approach those of full hydration. Up to a point, increased susceptibility toward solid-phase aggregation with increasing hydration has been observed in several systems. However, at higher water content, less aggregation is observed because of the dilution effect. Also, dilution of proteins with polymers of various functionalities, such as polyethylene glycol, dextran, diethylaminoethyl dextran, and carboxymethyl cellulose, significantly increase the stability of the protein and reduces the solid-phase aggregation.

One general way to stabilize proteins against solid-state aggregation is to control the water content in the solid formulation and maintain the water activity in the solid protein at optimal levels. This level depends on the nature of the protein, but in general, proteins maintained below their "monolayer" water coverage will exhibit superior solid-state stability. However, when solid proteins are suspended within a polymeric matrix intended for sustained release, the control of water activity is not always straightforward. According to current FDA requirements, an acceptable protein drug containing pharmaceutical product should exhibit less than 10% deterioration after 2 years.—Cleland, J. L. and Langer, R. In formulation and delivery of proteins and peptides, ACS books, 1994.

However, as is clear from the above description, the known means for providing microencapsulated protein containing DDS devices present some positive features, but are disadvantageous in that the fabrication procedures are complex and organic solvents are usually required during the microencapsulation process. Moreover these procedures may adversely affect the stability of peptide and protein drugs. For example, when fabricating microspheres using a polylactic acid copolymer, such as shown in U.S. Pat. No. 4,745,160, a mixture of dioxane and water is used. A dispersion is formed because the polylactic acid and/or the polypeptide are not completely dissolved in the mixture. Instead of dioxane and water, glacial acetic acid can also be used as a solvent. In either event the dispersion is lyophilized to obtain a powder. The powder can then be subjected to heat and pressure for preparation as a film, sheet, cylinder, or pulverized product thereof.

From the above it is evident that the prior art does not teach formulations of biodegradable polymeric microspheres without using an organic solvent and/or compression moulding techniques.

As previously noted, many microencapsulation processes require the use of organic solvents. There are some concerns about the toxicity of residual solvents, especially when chlorinated solvents (e.g., methylene chloride, chloroform) are used during the microencapsulation process. Structural and pharmacological denaturation as well as the loss of biological activity are commonly observed when large molecular weight polypeptides are in contact with organic solvents.

OBJECTS AND SUMMARY OF THE INVENTION

It is an object of the present invention to provide DDS comprising biodegradable copolymeric drug containing microspheres using a process where the use of an organic solvent is not required during the microencapsulation process.

It is also an object to provide DDS biodegradable copolymeric peptide drug containing microspheres that is applicable to polypeptides quite generally, but is most useful for polypeptides which are relatively stable at high temperature at around 50° C. in the solid state.

A further object is to provide a copolymer which can be processed into microspheres at temperatures below 100° C., and is thus suitable for the fabrication of microspheres incorporating heat sensitive or solvent sensitive peptide and protein drugs.

These and other objects which will become apparent may be accomplished by a process which comprises preparing a melt of polypeptides and an appropriate biodegradable block copolymer mixture to form a generally homogeneous drug copolymer mixture, dispersing the mixture in an appropriate fluid medium such as air, water or an oil, without using any organic solvent, to form microdroplets, and then cooling the fluid medium to solidify the microdroplets into microspheres and collecting the microspheres containing polypeptides uniformly dispersed therein. The resulting biodegradable microspheres are suitable as implantable or injectable pharmaceutical formulations. Following administration as solid microspheres, the formulations absorb water from the body to form a hydrogel from which the polypeptide is released continuously over an extended period of time with the concurrent or subsequent biodegradation of the copolymer.

Generally speaking, the drug loading in the microspheres will range from about 0.1 to 10% by weight with ranges of about 1 to 5% being preferred. However, strict numerical limitations are not critical provided the combination of drug with the copolymer is functional. Therefore, if higher drug loading can be accomplished for any given drug and copolymer combination, it is to be considered within the scope of the invention. Thus, the term "effective amount" when used in reference to the amount of drug loaded onto or admixed with a copolymer to form a melted mixture means that amount which the copolymer can contain and still form acceptable microspheres.

The temperature of incorporation of polypeptide and/or protein drugs into a polymeric matrix is extremely important to the life or activity of the drug. Even if the lyophilized state of a polypeptide or protein is in the native conformation, unfolding may still occur if the temperature exceeds the melting temperature (Tm) of the protein. For solid proteins, the Tm decreases significantly with increasing water content. In other words, the peptide/protein drugs should preferably be handled in a dry state and at temperatures below its melting point or range.

The melt blending process based on the ABA block copolymers described in the present invention meets these objectives. It has been found that, block copolymers of hydrophilic polyethylene glycol (B block) and biodegradable amorphous hydrophobic polymers (A block), having a glass transition temperature above 37° C., are particularly useful, because the polyethylene glycol B block plasticizes the hydrophobic A block, resulting in a material that can be readily processed at relatively low, sometimes even at ambient, temperatures. On subsequent standing the polyethylene glycol block crystallizes to give a tough hard product which can be easily handled for purposes of packaging, distribution and administration. In the alternative, BAB block copolymers can also be utilized wherein the end blocks are hydrophilic and the center A block is a biodegradable amorphous hydrophobic polymer. Further, branched and grafted ABA or BAB block copolymers may also be used.

DETAILED DESCRIPTION OF THE INVENTION

As used herein the following terms shall have the assigned meanings:

"Biodegradable" meaning that the block polymer can break down or degrade within the body to non-toxic components after all drug has been released.

"Drug" shall mean any organic compound or substance having bioactivity and adapted or used for a therapeutic purpose.

"Peptide", "polypeptide", "oligopeptide" and "protein" shall be used interchangeably when referring to peptide or protein drugs and shall not be limited as to any particular molecular weight, peptide sequence or length, field of bioactivity or therapeutic use unless specifically stated.

"Poly($\alpha$-hydroxy acid)" shall mean a poly($\alpha$-hydroxy acid) polymer per se or a poly($\alpha$-hydroxy acid) polymer or copolymer derived from the ring opening polymerization of an $\alpha$-hydroxy acid precursor, such as a corresponding lactide, glycolide or lactone.

According to the present invention, biodegradable microspheres comprising a pharmacologically useful polypeptide and a pharmaceutically acceptable ABA or BAB type non-crosslinked, amphipathic block copolymer are prepared without using organic solvents. The processing temperature can be lowered by employing low melting point block copolymers which effectively eliminates the need for employing solvents. Thus, there is no need for concern about residual solvents. Better drug release profile is attained from such microspheres as compared to the microparticles prepared by compression molding/grinding method techniques.

Biodegradable, Low Melting Temperature Polymeric Materials

The block copolymers utilized in this invention form a thermoplastic biodegradable hydrogel which is a biodegradable hydrogel crosslinked via physical means.

Preferably these are ABA type low melting biodegradable block copolymers made up of a hydrophilic B block segment contained between hydrophobic, biodegradable A block segments.

The hydrophilic or B block will preferably have an average molecular weight of between about 1,000 to 20,000 and is preferably between about 1,000 and 5,000. The total molecular weight of the copolymer should be between about 2,000 to about 50,000 in order to maintain its integrity at room temperature and still have low melting point.

The hydrophilic B block segment is preferably polyethylene glycol (PEG). The biodegradable hydrophobic, or A block, segment is a member selected from the group consisting of poly($\alpha$-hydroxy acids) and polyethylene carbonate.

The average molecular weight of such poly($\alpha$-hydroxy acid) polymeric blocks is between about 500 and 10,000 and is more preferably between about 500 and 3,000. The average molecular weight of enzymatically degradable polyethylene carbonate polymeric blocks is between about 200 and 10,000 and is more preferably between about 200 and 3,000.

The poly($\alpha$-hydroxy) polymer block is preferably a member derived or selected from the group consisting of poly(d,l-lactide), poly(l-lactide), poly(d,l-lactide-co-glycolide), poly(l-lactide-co-glycolide), poly($\epsilon$-caprolactone), poly($\gamma$-butyrolactone), poly($\delta$-valerolactone), poly($\epsilon$-caprolactone-co-lactic acid), poly($\epsilon$-caprolactone-co-glycolic acid-co-lactic acid), hydroxybutyric acid, malic acid and bi- or terpolymers thereof.

These copolymers are biodegradable and biocompatible. Polyethylene glycol, polylactide and lactide/glycolide copolymers are approved by FDA for medical use. Thermoplastic biodegradable hydrogels, such as these, are considered to have a microdomain structure of the so-called fringed micelle type: clusters of hard segments are dispersed in a continuous phase of soft segments to form the microdomains. These polymers have fringed micelle like structural properties because of amphiphilic property of the molecule. The multi-phase thus formed shows high physical strength without chemical crosslinking.

It is also possible to reverse the blocks and form a BAB block copolymer. BAB block copolymers are somewhat similar to the ABA block but differ in that the blocks are reversed, i.e. a BAB type block copolymer is synthesized such that the central or A block is made up of hydrophobic, biodegradable polymers and both B end blocks are hydrophilic polymers such as polyethylene glycol (PEG). The degradation pathway of poly($\alpha$-hydroxy acid) A blocks are well known and their metabolites are known to be nontoxic. Hydrophilic B blocks of PEG are water-soluble polymers, which are known to be non-toxic and readily excreted from the body. Therefore, a sustained dosage delivery form can be prepared by the use of these BAB triblock copolymers, in which a drug and polymer are melted together to form a molten mixture which is then processed into microspheres as described herein.

The copolymers will preferably contain about 60 to 90 percent by weight of the hydrophobic A block segments and about 10 to 40 percent by weight of the hydrophilic B block segments.

Additionally, the release profile of either ABA or BAB drug laden polymers may be further adjusted. For example, additional carboxyl functional groups can be incorporated into the hydrophobic block segment, thus such acidic groups can interact with basic groups of peptide/protein drugs. For example, incorporation of carboxyl groups can be achieved by employing malic acid or its derivatives as a comonomer in the hydrophobic blocks. Therefore, a more extended sustained release can be achieved because of the specific drug-polymer interaction.

Peptide/protein Drugs

The temperature employed during the encapsulation process is relatively low, i.e. in the range of between about 40° and 100° C. and most preferably between about 40° and 65° C. This invention is therefore applicable to polypeptides quite generally, but is most useful for polypeptides which are relatively stable in the solid state at temperatures within the above stated range.

Many labile peptide and protein drugs can be subjected to the melt encapsulation process described herein provided they are kept in a primarily dry (i.e. non-aqueous) environment during the process.

While not being specifically limited to the following, pharmaceutically useful polypeptides may be selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, coilstins, tyrocidin, gramicidines, and synthetic analogues, modifications and pharmacologically active fragments thereof, monoclonal antibodies and soluble vaccines.

The only limitation to the peptide or protein drug which may be utilized is one of functionality.

In some instances, the functionality or physical stability of proteins can also be increased by various additives to aqueous solutions of the peptide or protein drugs. Additives, such as polyols (including sugars), amino acids, proteins such as collagen and gelatin and certain salts may be used. It is clear that certain additives, in particular sugars and other polyols, impart significant physical stability to lyophilized proteins. These additives can be used to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices. Incorporation of sucrose within a sustained release formulation stabilize proteins against solid-state aggregation in humid atmospheres at elevated temperatures. Proteins such as gelatin and collagen serve as stabilizing or bulking agents to reduce denaturation and aggregation of unstable proteins. These additives can readily be incorporated into the present melt process of the present invention. For example, the polypeptides microparticles can be prepared by simply lyophilizing or spray drying the drug solution containing those additives described above. Sustained drug release can be obtained over an extended period of time. The release can be further modified by altering the formulation to include mannitol, sodium chloride, etc.

Developments in protein engineering may provide the possibility of increasing the inherent stability of peptide or proteins also. While such resultant engineered or modified proteins may be regarded as new entities in regards to regulatory implications, that does not alter their suitability for use in the present invention. One of the typical examples of modification is PEGylation of polypeptides. The stability of the polypeptide drugs can be significantly improved by covalently conjugating water-soluble polymers such as polyethylene glycol with the polypeptide. Another example is the modification of the aminoacid sequence in terms of the identity or location of one or more residues by terminal and internal addition and deletion or substitution (e.g., deletion of cysteine residues or replacement by alanine or serine).

Any improvement in stability enables a therapeutically effective polypeptide or protein to be continuously released over a prolonged period of time following a single administration of the pharmaceutical composition to a patient.

PREPARATION OF ABA COPOLYMERS

Poly (l-Lactide) homopolymer (PLA) is a crystalline polymer having a melting point of about 150°–160° C. On the other hand, PCL homopolymer is a semi-crystalline polymer having melting point at 63° C. Therefore, the lower melting PCL will generally be the more suitable "A" block polymer for making ABA copolymers for encapsulating peptides and proteins at lower temperatures. In order to use PLA as the "A" block polymer, the use of an amorphous poly (di-l-Lactide), lower molecular weights of PEG-PLA copolymers, preferably in the M.W. range of 2000 to 15,000, are required.

In the present invention, in order to obtain copolymers which maintain their integrity at room temperature and still have a low melting point, the molecular weight of the hydrophilic middle "B" block should be adjusted to a range of between about 1000 and 20,000 and the total molecular weight of the copolymer should also be adjusted to be within a range of between about 2,000 to 50,000.

In order to be suitably formed into microspheres the viscosity of the melted copolymer blend at the processing temperature should be in the range of about 1 to 80 poise and preferably not more than about 50 poise. However, the only limitation is one of functionality. If the viscosity of drug/copolymer the melt enables the formation of suitably sized microspheres when formed according any of the embodiments of the invention, the particular numerical viscosity reading or range is not to be considered as a limitation.

These block copolymers can be synthesized at a high yield (i.e. >95%) under the polymerization conditions exemplified below (130° C., 10 hrs). Table 1 shows compositions and some physical parameters of certain block copolymers used in the present invention to make microspheres.

TABLE 1

PEG-PCL block copolymerization (130° C., 10 hrs)

| Code | Feed composition (PCL-PEG-PCL) | Copolymer composition | Melting Point (°C.) |
|---|---|---|---|
| EC-3L-3-1 | 500-1000-500 | | |
| EC-3L-3-2 | 1000-1000-1000 | 1040-1000-1040 | 46.7 |
| EC-3L-3-3 | 1500-1000-1500 | | |
| EC-3L-3-4 | 2000-1000-2000 | 2230-1000-2230 | 56.6 |
| EC-3L-3-5 | 2500-1000-2500 | | |
| EC-3L-4-1 | 3000-1000-3000 | 3210-1000-3210 | 58.4 |
| EC-3L-4-2 | 4000-1000-4000 | | |
| EC-3L-4-3 | 5000-1000-5000 | 5220-1000-5220 | 61.1 |
| EC-3L-4-4 | 6000-1000-6000 | | |
| EC-3L-5-1 | 2000-1000-2000 | 2010-2000-2010 | 60.4 |
| EC-3L-5-2 | 4000-1000-4000 | 3730-2000-3730 | 62.3 |
| EC-3L-5-3 | 6000-1000-6000 | 5280-2000-5280 | 62.7 |
| EC-3L-5-4 | 8000-1000-8000 | 8990-2000-8990 | 61.9 |
| EC-3L-5-5 | 10000-1000-10000 | 9750-2000-9750 | |

The composition and molecular weight of the block copolymers were measured using 1H-NMR (Bruker 300 MHz). The melting point and thermal behavior was measured by differential scanning calorimetry (DSC 7 (Perkin Elmer)). The morphology of the microspheres prepared were examined by using scanning electron microscope (Stereoscan 360 (Cambridge Instruments, U.K.)). The melt viscosity of the copolymers were measured by using rheometer (Dynamic Spectrometer (Rheometrics, Inc.)). do we know what the melt viscosity of these polymers is??

EXAMPLE 1

Synthesis of PEG-PCL Block Copolymers
Method (a)

The PCL-PEG-PCL block copolymers of Table 1 were prepared by ring opening polymerization of ε-caprolactone (PCL) in the presence of polyethylene glycol (PEG). PEG of molecular weight 1000 was stirred and heated under vacuum at 120° C. for 3 hours and 0.1 wt % stannous octoate was added as a catalyst. Stannous octoate was diluted in toluene and the toluene was removed under vacuum. The specified amount of ε-caprolactone was added and the mixture was melt polymerized under a nitrogen atmosphere at 130° C. The mixture was maintained at 130° C. for 10 hrs, and then cooled and dissolved in chloroform. The chloroform solution was added to vigorously stirred methanol or diethyl ether, and the precipitate was filtered off, and dried in a vacuum oven for 3 hours at room temperature, then overnight at 40° C. The dried precipitate obtained was in the form of a fine powder, i.e. particles of about 100 μm.

Method (b)

As an alternative method, PEG of molecular weight 1000 was first dried by azeotropic distillation in benzene. The PEG was recovered and the procedure of Method (a) was then followed. In this case, a higher conversion rate of copolymer was obtained under the same conditions as in Method (a).

EXAMPLE 2

Synthesis of PEG-PLA Block Copolymers

PLA-PEG-PLA block copolymers were prepared by ring opening polymerization of lactide in the presence of polyethylene glycol (PEG). PEG of molecular weight 1000 was stirred and heated under vacuum at 120° C. for 3 hours and 0.1 wt % stannous octoate was added as a catalyst. Stannous octoate was diluted in toluene and the toluene was removed under vacuum. Sufficient amounts of lactide of a specified molecular weight were added to form the end blocks and the mixture was melt polymerized under a nitrogen atmosphere at 130° C. The mixture was maintained at 130° C. for 10 hrs, and then cooled and dissolved in chloroform. The chloroform solution was added to vigorously stirred methanol or diethyl ether, and the precipitate was filtered off, and dried in a vacuum oven for 3 hours at room temperature, then overnight at 40° C. Two copolymers, EL-3L-7-1 (PLA-PEG-PLA, 1000:1000:1000) and EL-3L-7-3 (PLA-PEG-PLA, 3000:3000:3000) comprising PLA end blocks of 1000 and 3000 molecular weight respectively and a center PEG block of 1000 were formed and are further referenced herein.

EXAMPLE 3

The relationship between melt viscosity, molecular weight, and melting temperature of block copolymers EC-3L-3-1 and EC-3L-3-2 of Table 1 and EL-3L-7-1, of Example 2 were measured. It was found that viscosity decreases with decreasing molecular weight or increasing temperature. At the same molecular weight and composition, the PLA-PEG-PLA block copolymer has a higher viscosity than the corresponding PCL-PEG-PCL block copolymer. These findings are beneficial for optimization of microsphere preparation conditions by a spray congealing process.

General Description of the Melt Process

The polypeptide or protein drugs are prepared as very fine microparticles by freeze drying followed by jet pulverizing or by spray drying of an aqueous solution with or without appropriate excipients or stabilizers. Any suitable state of the art process may be utilized which provides a low moisture, stable powdered form of the peptide or protein drug.

The protein drug is then intimately admixed into the block copolymer at temperatures above the melting point of the block copolymer. The drug powder may be suspended into a block copolymer melt or the drug powder and particles of the block copolymer may be admixed first and then melted together. In either event a substantially fluid molten homogeneous mixture of drug and copolymer is formed having a suitable low viscosity that microdroplets of the molten mixture can be formed. Air bubbles which might be incorporated during this mixing step are removed, preferably by vacuum.

Once the molten drug-polymer mixture is formed it can be dispersed in various ways into a fluid medium.

If the fluid medium is in the gaseous state, such as air, microdroplets can be dispersed into the gaseous environment in using various dispersing means. Representative of these are a pneumatic spray nozzle, a centrifugal extrusion head and a rotating disk, each of which are commercially available and are more fully explained and illustrated in the following description and examples.

EXAMPLE 4

Preparation of Microspheres by Melt Spraying

A prototype melt sprayer, was utilized to make microspheres without using water or organic solvent. The melt sprayer used was essentially a combination of an extruder and air sprayer. In this prototype, the molten material fed through the port was directly pushed to the heated spray nozzle compartment using plunger (5 mm diameter rod) driven by motor. As the molten drug and polymer mixture is extruded into the pneumatic spray nozzle the pressurized preheated air disperses the melt into the air or other gaseous environment where the molten microdroplets are solidified.

EXAMPLE 5

Preparation of Microspheres Using a Centrifugal Extrusion Head

The drug-block copolymer melt can be dispersed into air or other gaseous surroundings to make microdroplets by using a centrifugal extrusion head the one used for microencapsulation by throwing the shell and filler materials outward from the nozzles rotating at high speed (Southwest Research Institute). Because of the high speed rotation of the extrusion head, the viscous polymer melt is forced out through the nozzle by centrifugal force and the droplets are dispersed into the air.

EXAMPLE 6

Preparation of Microspheres Using a Rotating Disk

The drug-block copolymer melt can also be dispersed into air by using rotating disk. A thin layer of the polymer melt is formed on the hot surface of the disk which rotates at a very high speed, e.g. 3,000–15,000 rpm, and broken down into small droplets and dispersed. To prevent solidification of the drug-polymer melt, the rotating disk should be heated electrically or by localized hot air or infrared (IR) irradiation.

The particle size of the microspheres prepared by the centrifugal extrusion head or rotating disk embodiments might be somewhat larger than that of the microspheres prepared by pneumatic spray method. However, these processes are similar in that are continuous, easily scaled-up, and the resulting microspheres can also be used, not only for injection and implantation, but also for some other applications such as oral delivery of peptide and protein drugs.

In all of the above embodiments the viscosity of the polymer melt was in the range of about 20 to 80 poise and the dispersed droplets are cooled in the air or another gaseous environment to harden the microspheres. Sufficient contact time is provided to remove ample heat from the molten microspheres to solidify them before impacting each other or the surface of a collection device. The drug-polymer microspheres are then collected using conventional techniques for recovering solids particulates from a gaseous environment such as a cyclone or collection cone.

If desired the solid drug-polymer microspheres can be sized by sieving, gravity separation, sonication or other appropriate means and can also be sterilized by electron beam or gamma irradiation. If necessary the entire process can be carried out in a closed system or in a clean room.

As an alternate to dispersing microdroplets of molten drug-polymer into air or another gaseous environment, the dispersing fluid can be a liquid in which the melted drug-polymer mixture is not soluble. The liquid can be either hydrophilic or hydrophobic and the drug containing polymeric microspheres formed become a dispersed phase in the liquid continuous phase. The molten drug-polymer mixture is added to the liquid maintained at a temperature above the melting point of the polymer. Since the continuous phase is a liquid which is a non-solvent for both the drug and the polymer, the molten drug and polymer phase is dispersed as microdroplets in the hot liquid by appropriate means such as sonication or mechanical stirring. The temperature of the hot liquid is then lowered below the melting point of the polymer to solidify the drug containing polymeric microparticles which are then collected by centrifuging, decanting, filtering or other appropriate means and further processed or purified. For example, separated particles can be washed with a suitable solvent such as hexane, diethyl ether and the like to remove any residual continuous liquid phase and then dried and further separated according to particle size.

EXAMPLE 7

Preparation of Microspheres by Melt Dispersion in Water

In this embodiment the molten drug containing block copolymer is dispersed by sonication into a continuous phase of distilled hot water which is heated above the melting temperature of the polymer. The microspheres are formed by cooling water phase by appropriate means below the melting point of the polymer, e.g. with ice water. The solidified particles can then be separated by centrifugation, e.g. at 15,000 rpm for 30 minutes and then freeze dried.

EXAMPLE 8

Preparation of Microspheres by Melt Dispersion in 2% PVA Aqueous Solution

The same procedure as in Example 7 is carried out by using 2% aqueous polyvinyl alcohol (PVA) solution instead of the distilled water as a continuous medium. The shape and morphology of the microspheres are significantly improved by adding PVA into the aqueous medium.

EXAMPLE 9

Preparation of Microspheres by Melt Dispersion in Olive Oil

Essentially the same procedure as in Example 7 is followed except that hot olive oil is used as the continuous phase. The copolymer was dispersed by sonication into hot olive oil heated above the melting point of the polymer. The dispersion was cooled with ice water and the microspheres formed are collected by centrifugation, washed with diethyl ether, and then dried under reduced pressure.

The washing step that uses diethyl ether can be eliminated if the microsphere suspension in the oil is used directly for injection, implantation or oral administration without further processing. In such instances a sterile oil such as cottonseed oil, peanut oil, sesame oil, castor oil, soybean oil, or hydrogenated vegetable oil, suitable for injection can also be used and the processing can be carried out in a clean room or other sterile environment. In such instances, the microsphere concentration in the continuous oil phase will generally be in the range of about 10 to 50% w/v. This can be attained either by forming the microspheres at the desired concentration or adding or removing oil as needed to arrive at the preferred injectable concentration.

Table 2 shows the conditions for preparation of microspheres by melt dispersion method using distilled water, PVA aqueous solution (2 w/v %), and olive oil as a medium.

TABLE 2

Microsphere preparation by melt dispersion in liquids

| Polymer Code | Medium | Polymer Conc. (W/V %) | temp. | Remarks |
| --- | --- | --- | --- | --- |
| EC-3L-3-2 | water | 0.25 | 65° C. | −[1] |
| EC-3L-3-4 | water | " | " | −[1] |
| EC-3L-4-1 | water | " | " | ++[3] |
| EC-3L-3-2 | PVA solution (2%) | " | " | −[1] |
| EC-3L-3-4 | PVA solution (2%) | " | " | +[2] |
| EC-3L-4-1 | PVA solution (2%) | " | " | +++[4] |
| EC-3L-3-2 | Olive oil | " | " | +++[4] |

[1] "−" means very poor microsphere formation, large aggregates
[2] "+" means fair microsphere formation with some aggregation
[3] "++" means irregularly shaped microspheres, no aggregation
[4] "+++" means good spherical discrete microspheres formed No acceptable microspheres were formed when the PEG block content of the copolymer was 33% (EC-3L-3-2). However, smooth surfaced spherical microspheres were formed when the PEG block content of the copolymer was 14% (EC-3L-4-1). The particle size was measured by SEM to be 10–20 μm with very narrow size distribution. When olive oil was used as the liquid medium, good spherical microspheres were formed even with PEG block content of 33%. The differences in microsphere formation may be explained in that the block copolymer having high PEG content will not phase separate well in water due to the hydrophilicity of PEG moiety. On the other hand, a high PEG content does not cause any problem in a hydrophobic liquid such as olive oil. When minor amounts of PVA were added into the aqueous medium, the microsphere formation was dramatically improved. While the reasons are not know for sure it was probably because of the improved stability of emulsion formed at 65° C. due to the increased viscosity and prevention of aggregation in the presence of PVA.

The above examples have been directed primarily to the preparation of block copolymer microspheres per se. The following examples utilize the technology shown in the preceding examples wherein a specific protein or peptide drug has been combined with the block copolymer in a melt process.

EXAMPLE 10

Bovine serum albumin (BSA) is ground into fine microparticles by using an air jet pulverizer and collected using a minicyclone unit. Dehumidified compressed air, at a pressure of 100 psig, is used as the air jet source for the pulverizer operation. The microparticles collected in the container attached to the minicyclone unit are recirculated to the feeding port and the pulverization operation is continued until the particle size of the BSA is below 5 μm.

Ten grams of the powdered block copolymer (EC-3L-3-2, PCL:PEG:PCL=1000:1000:1000) described in Example 1 is admixed together with 1 gram of these BSA microparticles and the admixture is fed into the melt sprayer described in Example 4. A uniform mixture of BSA block copolymer is formed containing about 9% by weight BSA. Compressed air (100 psig) preheated at 60° C. is used to prevent any significant viscosity increase in the melt sprayer due to cooling. Small microdroplets of the molten BSA-block copolymer are dispersed into the air and are solidified. The solidified droplets having an average particle size of about 20 μm are gravitationally collected onto a stainless steel plate.

EXAMPLE 11

A one gram sample of the BSA microparticles from Example 10 are admixed with ten grams of the block copolymer (EL-3L-3-2) powder of Example 1. The mixture of the BSA protein and copolymer particles are fed into the extruder part of the melt sprayer described in Example 4. No compressed air is used in this example. The tip of the spray nozzle is positioned directly above a disk having a diameter of 3 cm and rotating at 5000 rpm five feet above the floor level. The area of the rotating disk and extruder is illuminated with an infra red (IR) lamp to maintain heat in the area of about 65° C. and prevent viscosity increase of the BSA block copolymer melt as it exits the nozzle. The drug polymer melt, having a viscosity of about 80 poise is dispersed from the nozzle head as a stream onto the surface of the rotating disk. The high speed of rotation causes the melt to be flung from the disk surface as microdroplets into the surrounding space where the BSA polymer droplets are cooled as they fall by gravitational force to the floor onto a stainless steel plate for collection.

The speed of rotation of the disk can be adjusted according to the viscosity of the drug polymer melt and the size of the microdroplets to be formed. At higher viscosities, higher rotational speeds will be required to maintain the same droplet size. Increasing the rotational speed while maintaining the same viscosity will result is smaller microparticles being formed.

EXAMPLE 12

This example illustrates the preparation of zinc insulin microspheres by melt dispersion in water. Ten milligrams of microcrystalline zinc insulin (PENTEX recombinant human insulin Zinc salt) and block copolymer (EL-3L-4-1, PCL-PEG-PCL=3,000:1,000:3000) particles obtained in Example 1 are blended together at approximately 50° C. to form a homogeneous mixture of the insulin drug in the block copolymer. The resulting opaque mass is added to distilled water, preheated to 65° C. and adjusted to a pH of 5.3 (the isoelectric point of the insulin), and vigorously homogenized using a T.K. Homomixer Mark II at a speed of 10,000 rpm to form a dispersion of the insulin polymer particles in a continuous water phase. Immediately following the homogenization, the medium is transferred to an ice bath and cooled using gentle stirring causing the particles to solidify. The solidified microspheres are separated via centrifugation at 5,000 rpm for 10 minutes and then freeze dried.

EXAMPLE 13

This example illustrates the preparation of zinc insulin microspheres by melt dispersion in 2% PVA solution. Ten milligrams of the microcrystalline zinc insulin and the block copolymer particles as used in Example 12 are blended together at approximately 50° C. to form a homogeneous mixture of the insulin drug in the block copolymer. The resulting opaque mass is added to 2% aqueous polyvinyl alcohol (PVA 88 mol % hydrolyzed, molecular weight 7,000) solution, preheated to 65° C. and adjusted to a pH of 5.3 (the isoelectric point of the insulin) to further reduce leaching of the insulin protein during the process, and vigorously agitated by sonication using a Branson Sonifier 250 to form a dispersion of the insulin polymer particles in a continuous PVA aqueous phase. Immediately following the sonication, the medium is transferred to an ice bath and cooled using gentle stirring causing the particles to solidify. The solidified microspheres are separated via centrifugation at 5,000 rpm for 10 minutes, washed with distilled water and then freeze dried.

Leaching of a water soluble protein drug during the microsphere preparation in water such as is shown in Example 12 or in 2% PVA as is shown in Example 13 can possibly present a disadvantage. However, leaching can be reduced or eliminated and drug loading can be significantly increased by utilizing water-insoluble or poorly water-soluble salt forms of the proteins. For example, protein salts forms can be prepared using rare earth metals such as $Zn^{+2}$, $Co^{+3}$, $Ni^{+2}$, $Cu^{+2}$, $Fe^{+2,+3}$, etc. or hydrophobic compounds such as fatty acids, phospholipids, etc.

EXAMPLE 14

One hundred (100) milligrams of human calcitonin (molecular weight 3,500) is dissolved in 100 mls of 1 (w/v) % gelatin solution and sterile filtered through a 0.22 μm membrane filter. The solution is spray dried by using a Buchi mini sprayer dryer having an inlet temperature of 120° C. and an outlet temperature of 80° C. The nozzle body of the dryer is cooled with circulating water to prevent denaturation of the calcitonin protein. The microparticles (particle size range of 1–10 μm are collected in the cyclone portion of the dryer which is water jacketed to prevent prolonged exposure of the spray dried particles to high or denaturation temperatures.

EXAMPLE 15

One hundred (100) milligrams of the fine microparticles of human calcitonin obtained in Example 14 are blended with 0.9 grams of the block copolymer (EL-3L-3-2) powder of Example 1 at approximately 50° C. to obtain an homogeneous blend of the calcitonin protein and block copolymer. The blended mass is added into a vegetable oil continuous phase preheated to about 60° C. The calcitonin and copolymer blend is melted by the heated vegetable oil which is then vigorously agitated by sonication using a Branson Sonifier 250 to form a milky suspension comprising microdispersions of calcitonin copolymer in the heated oil. The container holding the suspension is transferred to an ice bath where the suspension is gently stirred with a propeller stirrer. Upon cooling the microdispered droplets solidify into calcitonin copolymer microspheres. The microspheres are collected by centrifugation at 3000 rpm, washed with hexane and air dried. The resulting microspheres contain about 0.9% w calcitonin.

EXAMPLE 16

The procedure of Example 15 is repeated utilizing a hydrogenated vegetable oil (Miglyol) as a suspending or continuous phase medium. The Miglyol is sterilized before use and the entire procedure is carried out in a clean room. Following sonication and cooling, the solidified calcitonin microspheres are collected by means of centrifugation at 5,000 rpm for 10 minutes and then resuspended into a fresh sterile hydrogenated vegetable oil (miglyol). The microsphere concentration in the suspension is about 20% w/v. An 1 ml aliquot of the suspension, containing 1.8 mg of calcitonin is sealed in a vial which can be stored for used as an oil based injectable.

EXAMPLE 17

The procedures of Examples 10 and 11 are repeated using spray dried BSA microparticles in the place of the jet pulverized microparticles and similar results are obtained.

Dosage forms can be readily determined by one skilled in the art and will depend upon numerous factors and variants including the bioactivity of the peptide or protein drug, its molecular weight, solubility, stability. Therefore, no general statement as to dosage or dosage form will be applicable to all peptide or protein drugs. Of more relevance is the size of the microparticles which are formed. When formed in an oil or water for purposes of injection the particle size will generally range from about 1 to 100 μm and when formed for oral use in capsules or compressed tablets the size may be somewhat larger, e.g. from about 100 to 1000 μm.

In general, protein release profiles from microspheres of hydrophobic biodegradable polymers prepared by the prior art methods of spray drying, solvent extraction precipitation, solvent evaporation, and press grinding methods indicate that most of the protein is released before the polymer matrix loses weight, i.e. prior to degradation of the polymer. However, when using the ABA or BAB block copolymer systems employed in the present invention for a microsphere DDS a more constant sustained release can be expected. The loss of the hydrophilic PEG B block reduces the water content, and decreases the release rate of the protein. In contrast, the degradation of hydrophobic A block and the destruction of mechanical properties of the matrix increases the release rate of the protein. Thus, there is a counterbalancing in that the more rapid degradation of the polyester A block can compensate for the decrease in the release rate of protein produced by the loss of PEG B block. Even high molecular weight proteins can diffuse out from the block copolymer matrix because of the swelling of the polymer in water or physiological aqueous environment. The release rate can be controlled or optimized by changing the composition, molecular weights and relative proportion of the comonomer blocks of the block copolymers.

Concerning the drug, loss of native protein structure may result in aggregation via hydrophobic interactions or increased exposure of reactive groups. Depending upon the polymer matrix, protein will experience significant hydration within the polymeric matrix after a depot system has been implanted within a tissue site or following oral ingestion. It is possible to control the microenvironment of the protein within DDS by changing the matrix. Water contents within the polymer bulk in vitro can be as low as 1% for crystalline poly (l-Lactide) homopolymer, and up to 60% for amorphous poly(glycolic-co-lactic acid) (mole ratio 50:50). The choice of matrix material will afford not only control of water activity within the depot but also other important factors influencing aggregation, such as hydrophobicity and pH. Solid proteins embedded within polymeric systems exhibit superior stabilities compared with their behavior under otherwise identical conditions in solution. It is therefore generally desirable to maintain a native protein structure in the solid state to enhance stability. This stability may be further enhanced by increasing the hydrophobicity of the polymer to limit the water content within the device or by reducing the thickness of the device, thereby allowing for more rapid dissolution and, thus, a shorter time of hydration.

We claim:

1. A process for preparing microspheres of an admixture of a biodegradable low melting point block copolymer and a water soluble and heat resistant peptide/protein drug, which comprises:

(a) preparing a molten mixture of an effective amount of peptide/protein drug microparticles and a biodegradable block copolymer at a temperature above the melting temperature of said block copolymer;

(b) dispersing said molten mixture into a continuous fluid medium in such a manner as to form microdroplets of said molten mixture in said fluid medium;

(c) lowering the temperature of said microdroplets in a cooling environment below the melting point of said block copolymer to form solid microspheres; and (d) separating said microspheres from said continuous fluid medium.

2. A process according to claim 1 wherein said block copolymer has a melting point below about 100° C. and a molecular weight average of between about 2,000 and 50,000.

3. A process according to claim 2 wherein said block copolymer is a member selected from the group consisting of ABA and BAB block copolymers wherein said A block segment is a hydrophobic, biodegradable polymer and said B block segment is a hydrophilic polymer.

4. A process according to claim 3 wherein said block copolymer contains about 60 to 90 percent by weight of the hydrophobic A block segment and about 10 to 40 percent by weight of the hydrophilic B block segment.

5. A process according to claim 4 wherein the hydrophilic B block segment is polyethylene glycol having an molecular weight average of between about 1,000 to 20,000.

6. A process according to claim 5 wherein the hydrophobic A polymer block segment is a member selected from the group consisting of poly(α-hydroxy acids) and poly(ethylene carbonates).

7. A process according to claim 6 wherein the hydrophobic, biodegradable A block is a poly(α-hydroxy acid) having a molecular weight average of between about 500 and 10,000.

8. A process according to claim 7 wherein said poly(α-hydroxy acid) is a member derived or selected from the group consisting of poly (d,l-lactide), poly(l-lactide), poly(d,l-lactide-co-glycolide), poly(l-lactide-co-glycolide), poly(ε-caprolactone), poly(γ-butyrolactone), poly(δ-valerolactone), poly(ε-caprolactone-co-lactic acid), poly(ε-caprolactone-co-glycolic acid-co-lactic acid), hydroxybutyric acid, malic acid and bi- or terpolymers thereof.

9. A process according to claim 6 wherein the hydrophobic A block segment is a polyethylene carbonate having a molecular weight average of about 200 and 10,000.

10. A process according to claim 6 wherein said block copolymer is an ABA copolymer consisting of terminal hydrophobic, biodegradable A block segments and an inner hydrophilic B block segment.

11. A process according to claim 6 wherein said peptide/protein drug is a member selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines.

12. A process according to claim 6, wherein said continuous fluid medium is a gas and said molten mixture is dispensed by means of a member maintained at a temperature above the melting point of the block copolymer.

13. A process according to claim 12 wherein said means is a member selected from the group consisting of a pneumatic spray nozzle, a centrifugal extrusion head and a rotating disk.

14. A process according to claim 13 wherein said continuous fluid medium is air.

15. A process according to claim 13 wherein said molten mixture is dispensed by means of a pneumatic spray nozzle.

16. A process according to claim 13 wherein said molten mixture is dispensed by means of a centrifugal extrusion head.

17. A process according to claim 13 wherein said molten mixture is dispensed by means of a rotating disk.

18. A process according to claim 6 wherein said continuous fluid medium is a liquid immiscible with said molten mixture said liquid being maintained at a temperature above the melting temperature of said block copolymer and wherein said molten mixture is dispensed into said liquid by means that forms a dispersion.

19. A process according to claim 18 wherein said liquid is a member selected from the group consisting of silicone oil, olive oil, cotton seed oil, peanut oil, sesame oil, castor oil, soybean oil, hydrogenated vegetable oil, cone oil, whale oil, liquid paraffin, toluene, xylene and hexane.

20. A process according to claim 19 wherein said liquid is cooled below the melting point of said copolymer causing said molten mixture to harden into microspheres and separating said microspheres from said liquid.

21. A process according to claim 20 wherein said microspheres are separated from said liquid by means of centrifugation, filtration, or decantation.

22. A process according to claim 18 wherein said liquid is a sterile pharmaceutically acceptable injectable oil.

23. A process according to claim 12 wherein said member selected from the group consisting of olive oil, cotton seed oil, peanut oil, sesame oil, castor oil, soybean oil, and hydrogenated vegetable oil.

24. A process according to claim 23 wherein said dispersion is contained in a unit dosage form and contained in a sterile environment at a temperature below the melting point of said copolymer and wherein the concentration of said microspheres in said oil is between about 10 to 50% w/v.

* * * * *